United States Patent
Matsumoto

(10) Patent No.: US 12,310,787 B2
(45) Date of Patent: May 27, 2025

(54) ULTRASOUND DIAGNOSTIC APPARATUS AND CONTROL METHOD FOR ULTRASOUND DIAGNOSTIC APPARATUS CAPABLE OF PERFORMING URINARY ORGAN EXAMINATION ACCORDING TO GENDER OF SUBJECT

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 218 days.

(21) Appl. No.: 18/061,935

(22) Filed: Dec. 5, 2022

(65) Prior Publication Data
US 2023/0181155 A1  Jun. 15, 2023

(30) Foreign Application Priority Data
Dec. 13, 2021  (JP) .................................. 2021-201571

(51) Int. Cl.
*A61B 8/08* (2006.01)
*A61B 5/00* (2006.01)
*A61B 8/00* (2006.01)

(52) U.S. Cl.
CPC .......... *A61B 8/0866* (2013.01); *A61B 5/7267* (2013.01); *A61B 8/5223* (2013.01); *A61B 8/5292* (2013.01)

(58) Field of Classification Search
CPC .................................................. A61B 5/7267
See application file for complete search history.

(56) References Cited

U.S. PATENT DOCUMENTS

2008/0139938 A1* 6/2008 Yang ..................... G06T 7/0012
                                                          600/445
2011/0004101 A1* 1/2011 Yang ....................... A61B 8/14
                                                          600/443

(Continued)

FOREIGN PATENT DOCUMENTS

| JP | 2011-005025 A | 1/2011 |
| JP | 2020-519369 A | 7/2020 |

OTHER PUBLICATIONS

The extended European search report issued by the European Patent Office on Feb. 6, 2023, which corresponds to European Patent Application No. 22212906.6-1126 and is related to U.S. Appl. No. 18/061,935.

*Primary Examiner* — Keith M Raymond
*Assistant Examiner* — Nyrobi Celestine
(74) *Attorney, Agent, or Firm* — Studebaker Brackett PLLC

(57) ABSTRACT

There are provided an ultrasound diagnostic apparatus and a control method for an ultrasound diagnostic apparatus capable of performing an appropriate examination according to a gender of a subject without requiring a user to input the gender of the subject.

The ultrasound diagnostic apparatus includes: a bladder extraction unit that extracts a bladder region from an ultrasound image; a gender determination unit that determines a gender of a subject based on a shape of the bladder region in a case where an area of the extracted bladder region is larger than a predetermined area threshold value; and an observation support unit that supports an observation of a next observation site which is determined according to the determined gender of the subject.

20 Claims, 9 Drawing Sheets

(56) References Cited

U.S. PATENT DOCUMENTS

2018/0330518 A1* 11/2018 Choi ................ G06N 3/045
2020/0345324 A1   11/2020 Matsumoto et al.
2021/0219941 A1    7/2021 Tsutaoka
2021/0312652 A1   10/2021 Padwal et al.

* cited by examiner

ULTRASOUND DIAGNOSTIC APPARATUS AND CONTROL METHOD FOR ULTRASOUND DIAGNOSTIC APPARATUS CAPABLE OF PERFORMING URINARY ORGAN EXAMINATION ACCORDING TO GENDER OF SUBJECT

CROSS-REFERENCE TO RELATED APPLICATIONS

The present application claims priority under 35 U.S.C. § 119 to Japanese Patent Application No. 2021-201571, filed on Dec. 13, 2021. The above application is hereby expressly incorporated by reference, in its entirety, into the present application.

BACKGROUND OF THE INVENTION

1. Field of the Invention

The present invention relates to an ultrasound diagnostic apparatus and a control method for an ultrasound diagnostic apparatus, and particularly relates to an ultrasound diagnostic apparatus and a control method for an ultrasound diagnostic apparatus capable of performing an examination according to a gender of a subject.

2. Description of the Related Art

In related art, an ultrasound diagnostic apparatus using ultrasound images has been put into practical use in a medical field. In general, such an ultrasound diagnostic apparatus includes an ultrasound probe in which a transducer array is provided and a diagnostic apparatus main body connected to the ultrasound probe. An ultrasound beam is transmitted from the ultrasound probe toward a subject, an ultrasound echo from the subject is received by the ultrasound probe, and a reception signal is electrically processed, for example, in the diagnostic apparatus main body. Thereby, an ultrasound image is generated.

In a urinary organ examination, generally, a plurality of organs of a subject are continuously measured. Here, the organs to be measured differ depending on a gender of a subject. For example, in a case where the subject is a male, an examination is performed in order of measurement of a urine amount of a bladder, measurement of a prostate, and measurement of a kidney. In addition, in a case where the subject is a female, an examination is performed in order of measurement of a urine amount of a bladder, measurement of a uterus, and measurement of a kidney.

In addition, the organs to be measured and the measurement order of the plurality of organs may change depending on not only the gender of the subject but also a state of the organ of the subject. As a result, for an individual subject, measurement of some organs among the plurality of organs may be forgotten, or measurement of the same organ may be performed again as necessary.

JP2020-519369A discloses an ultrasound system that improves accuracy of organ extraction by modifying an extraction region from an ultrasound image based on a gender, an age, and the like of a subject by using, for example, assumption information related to a three-dimensional shape and a size of an organ such as a bladder.

SUMMARY OF THE INVENTION

However, in the system disclosed in JP2020-519369A, a user needs to input a gender, an age, and the like of a subject. In addition, in a case where there is an error in the input, there is a risk that assumption information that is inappropriate for the subject is used and thus accuracy of organ extraction is deteriorated.

The present invention has been made to solve such a problem in the related art, and an object of the present invention is to provide an ultrasound diagnostic apparatus and a control method for an ultrasound diagnostic apparatus capable of performing an appropriate examination according to the gender of the subject without requiring the user to input the gender of the subject.

In order to achieve the above object, according to an aspect of the present invention, there is provided an ultrasound diagnostic apparatus including: an image generation unit that generates an ultrasound image obtained by imaging a subject by transmitting and receiving ultrasound beams using an ultrasound probe; a bladder extraction unit that extracts a first region including a bladder region from the ultrasound image; a gender determination unit that determines a gender of the subject based on a shape of the bladder region in a case where a size of the first region extracted by the bladder extraction unit is larger than a predetermined size threshold value; and an observation support unit that supports an observation of a next observation site which is determined according to the gender of the subject determined by the gender determination unit.

The bladder extraction unit can extract the bladder region as the first region. Alternatively, the bladder extraction unit may extract, as the first region, any one of a region surrounded by a circumscribing rectangle that circumscribes the bladder region, a region surrounded by a circumscribing ellipse that circumscribes the bladder region, a region surrounded by a circumscribing circle that circumscribes the bladder region, a region surrounded by a rectangle including the circumscribing rectangle, a region surrounded by an ellipse including the circumscribing ellipse, or a region surrounded by a circle including the circumscribing circle.

The gender determination unit can determine the gender of the subject based on a curved shape of a lower edge of the bladder region included in the first region extracted by the bladder extraction unit.

For example, the gender determination unit may determine that the subject is a male in a case where a curvature radius of a portion at both ends of the lower edge of the bladder region is equal to or smaller than a predetermined curvature radius threshold value, and determine that the subject is a female in a case where the curvature radius of the portion at both ends of the lower edge of the bladder region is larger than the predetermined curvature radius threshold value.

Alternatively, the gender determination unit may determine that the subject is a male in a case where a center portion of the lower edge of the bladder region is downwardly curved in a recess shape, and determine that the subject is a female in a case where the center portion of the lower edge of the bladder region is downwardly curved in a protrusion shape.

Further, the gender determination unit can determine the gender of the subject by using a trained determination model obtained by learning shapes of bladder regions in ultrasound images obtained by imaging a bladder of a male and ultrasound images obtained by imaging a bladder of a female.

The ultrasound diagnostic apparatus further includes a reliability calculation unit that calculates a reliability of determination of the gender of the subject by the gender determination unit.

The observation support unit can be configured to notify a user of the reliability calculated by the reliability calculation unit.

In addition, preferably, the ultrasound diagnostic apparatus further includes a bladder size calculation unit that calculates an area of the bladder region included in the first region extracted by the bladder extraction unit.

Preferably, the ultrasound diagnostic apparatus further includes the ultrasound probe, an input device that allows a user to perform an input operation, and a monitor that displays the ultrasound image generated by the image generation unit.

The observation support unit can determine that the next observation site is a prostate in a case where the gender determination unit determines that the subject is a male, and determine that the next observation site is a uterus in a case where the gender determination unit determines that the subject is a female.

The observation support unit can guide the user to operate the ultrasound probe such that the next observation site is visualized on the monitor.

Preferably, the observation support unit guides the user to move the ultrasound probe in parallel or tilt the ultrasound probe such that the prostate is visualized on the monitor and to perform imaging of the ultrasound image in a case where the gender determination unit determines that the subject is a male, and guides the user to rotate the ultrasound probe by 90 degrees such that the uterus is visualized on the monitor and to perform imaging of the ultrasound image in a case where the gender determination unit determines that the subject is a female.

Preferably, the gender determination unit does not determine the gender of the subject in a case where the size of the first region extracted by the bladder extraction unit is equal to or smaller than the predetermined size threshold value.

In this case, the observation support unit can instruct the user to perform re-examination after a lapse of a predetermined time.

Alternatively, the observation support unit can also instruct the user to perform re-examination after an input of information related to the gender of the subject via the input device.

In addition, the observation support unit may instruct the user to find a section in which an area of the bladder region displayed on the monitor is increased by moving the ultrasound probe.

The observation support unit may be configured to automatically recognize the next observation site from the ultrasound image.

The observation support unit can notify the user of an error in a case where the gender of the subject that is determined by the gender determination unit is different from the gender based on subject information of the subject that is input via the input device.

According to another aspect of the present invention, there is provided a control method for an ultrasound diagnostic apparatus, the method including: generating an ultrasound image obtained by imaging a subject by transmitting and receiving ultrasound beams using an ultrasound probe; extracting a first region including a bladder region from the ultrasound image; determining a gender of the subject based on a shape of the bladder region in a case where a size of the extracted first region is larger than a predetermined size threshold value; and supporting an observation of a next observation site which is determined according to the determined gender of the subject.

According to the present invention, the bladder extraction unit extracts the first region including the bladder region from the ultrasound image, the gender determination unit determines the gender of the subject based on the shape of the bladder region in a case where the size of the first region is larger than the predetermined size threshold value, and the observation support unit supports an observation of the next observation site determined according to the gender of the subject. Thereby, it is possible to perform an appropriate examination according to the gender of the subject without requiring the user to input the gender of the subject.

DESCRIPTION OF THE PREFERRED EMBODIMENTS

Hereinafter, embodiments of the present invention will be described with reference to the accompanying drawings.

A description of components to be described below is based on a representative embodiment of the present invention. On the other hand, the present invention is not limited to such an embodiment.

Note that, in this specification, a numerical range represented by using "to" means a range including numerical values described before and after "to", both ends inclusive, as a lower limit value and an upper limit value.

In this specification, it is assumed that terms "identical" and "same" include an error margin which is generally allowed in the technical field.

Embodiment 1

Figure 1:
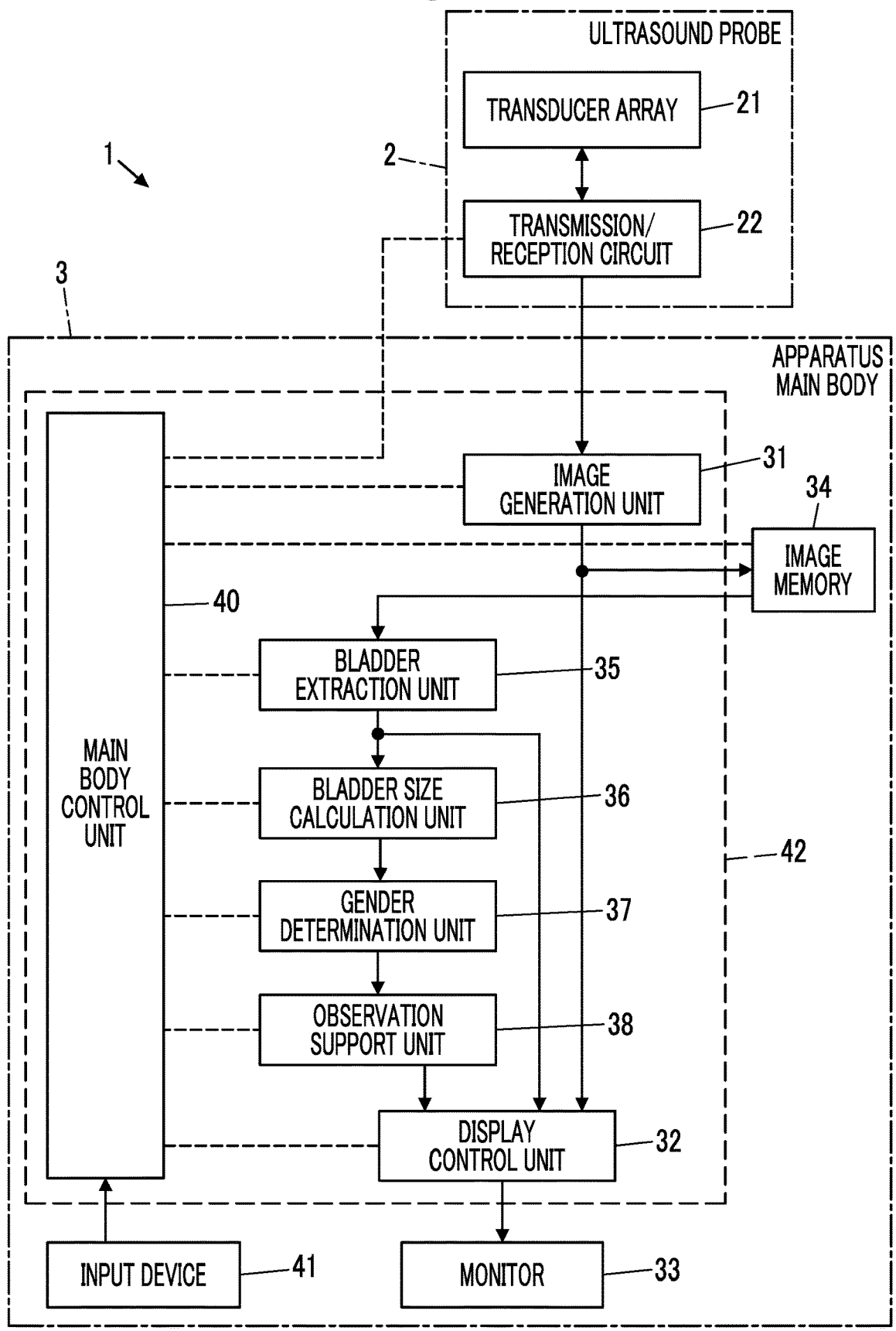
FIG. 1 is a block diagram illustrating a configuration of an ultrasound diagnostic apparatus according to an embodiment 1 of the present invention.

FIG. 1 illustrates a configuration of an ultrasound diagnostic apparatus 1 according to an embodiment 1 of the present invention. The ultrasound diagnostic apparatus 1 includes an ultrasound probe 2 and an apparatus main body 3. The ultrasound probe 2 and the apparatus main body 3 are wired-connected to each other via a cable (not illustrated).

The ultrasound probe 2 includes a transducer array 21 and a transmission/reception circuit 22 connected to the transducer array 21.

The apparatus main body 3 includes an image generation unit 31 connected to the transmission/reception circuit 22 of the ultrasound probe 2. A display control unit 32 and a monitor 33 are sequentially connected to the image generation unit 31, and an image memory 34 is connected to the image generation unit 31. Further, a bladder extraction unit 35, a bladder size calculation unit 36, a gender determination unit 37, and an observation support unit 38 are sequentially connected to the image memory 34, and the bladder extraction unit 35 and the observation support unit 38 are connected to the display control unit 32.

A main body control unit 40 is connected to the image generation unit 31, the display control unit 32, the image memory 34, the bladder extraction unit 35, the bladder size calculation unit 36, the gender determination unit 37, and the observation support unit 38. An input device 41 is connected to the main body control unit 40. In addition, the transmission/reception circuit 22 of the ultrasound probe 2 is connected to the main body control unit 40.

A processor 42 is configured by the image generation unit 31, the display control unit 32, the bladder extraction unit 35, the bladder size calculation unit 36, the gender determination unit 37, the observation support unit 38, and the main body control unit 40.

The transducer array 21 of the ultrasound probe 2 includes a plurality of ultrasound transducers which are one-dimensionally or two-dimensionally arranged. Each of these transducers transmits an ultrasound wave according to a drive signal supplied from the transmission/reception circuit 22, receives a reflected wave from a subject, and outputs an analog reception signal. Each transducer is configured by, for example, forming electrodes on both ends of a piezoelectric body such as a piezoelectric ceramic represented by lead zirconate titanate (PZT), a polymeric piezoelectric element represented by poly vinylidene di fluoride (PVDF), or a piezoelectric single crystal represented by a lead magnesium niobate-lead titanate (PMN-PT) solid solution.

Figure 2:
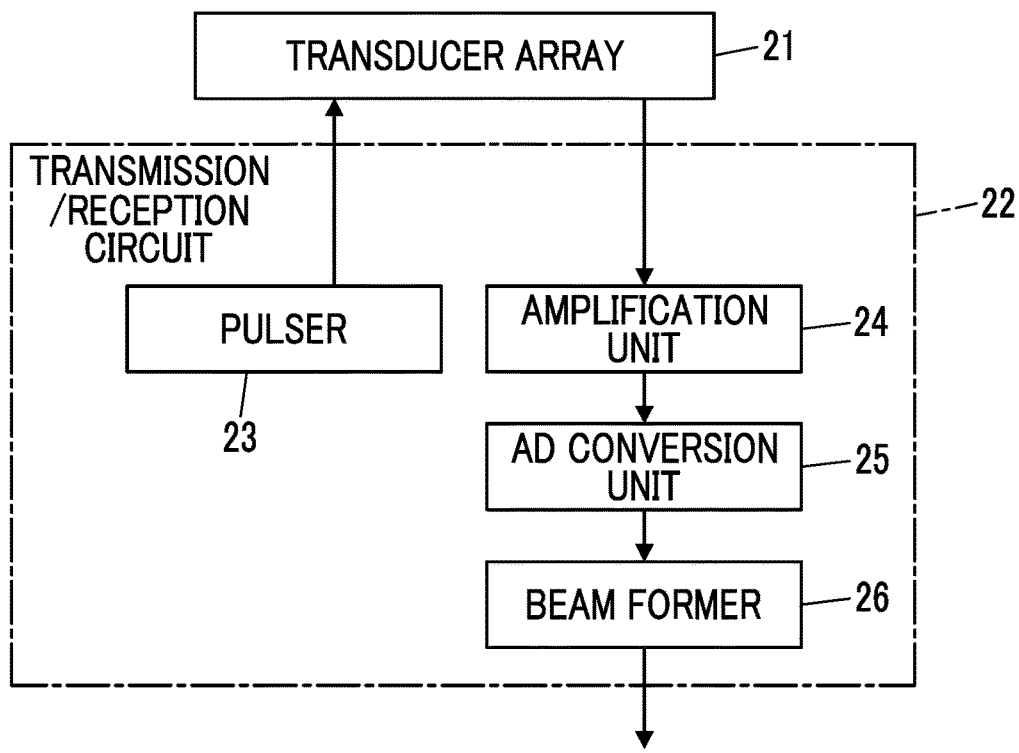
FIG. 2 is a block diagram illustrating an internal configuration of a transmission/reception circuit according to the embodiment 1 of the present invention.

The transmission/reception circuit 22 transmits an ultrasound wave from the transducer array 21 and generates a sound ray signal based on the reception signal acquired by the transducer array 21 under a control of the main body control unit 40. As illustrated in FIG. 2, the transmission/reception circuit 22 includes a pulser 23 connected to the transducer array 21, an amplification unit 24 sequentially connected in series to the transducer array 21, an analog-to-digital (AD) conversion unit 25, and a beam former 26.

The pulser 23 includes, for example, a plurality of pulse generators, adjusts a delay amount of each drive signal based on a transmission delay pattern which is selected according to a control signal from the main body control unit 40 such that ultrasound waves to be transmitted from the plurality of transducers of the transducer array 21 form ultrasound beams, and supplies each drive signal with the adjusted delay amount to the plurality of transducers. In this way, in a case where a voltage having a pulse shape or a continuous wave shape is applied to the electrodes of the transducers of the transducer array 21, the piezoelectric body expands and contracts. Thereby, ultrasound waves having a pulse shape or a continuous wave shape are generated from each transducer, and thus an ultrasound beam is formed from a composite wave of these ultrasound waves.

The transmitted ultrasound beam is reflected by an object such as a portion of a subject, and an ultrasound echo propagates toward the transducer array 21 of the ultrasound probe 2. The ultrasound echo which propagates toward the transducer array 21 in this way is received by each transducer included in the transducer array 21. At this time, in a case where the propagating ultrasound echo is received, each transducer included in the transducer array 21 expands and contracts. Thereby, a reception signal as an electrical signal is generated, and these reception signals are output to the amplification unit 24.

The amplification unit 24 amplifies the signal which is input from each transducer included in the transducer array 21, and transmits the amplified signal to the AD conversion unit 25. The AD conversion unit 25 converts the signal transmitted from the amplification unit 24 into pieces of digital reception data, and transmits the pieces of reception data to the beam former 26. The beam former 26 performs so-called reception focus processing by applying and adding a delay to each of the pieces of reception data which is converted by the AD conversion unit 25 according to a sound velocity or a sound velocity distribution which is set based on a reception delay pattern selected according to a control signal from the main body control unit 40. By this reception focus processing, a sound ray signal obtained by performing phasing addition on each of the pieces of reception data which is converted by the AD conversion unit 25 and narrowing down a focus of the ultrasound echo is acquired.

Figure 3:
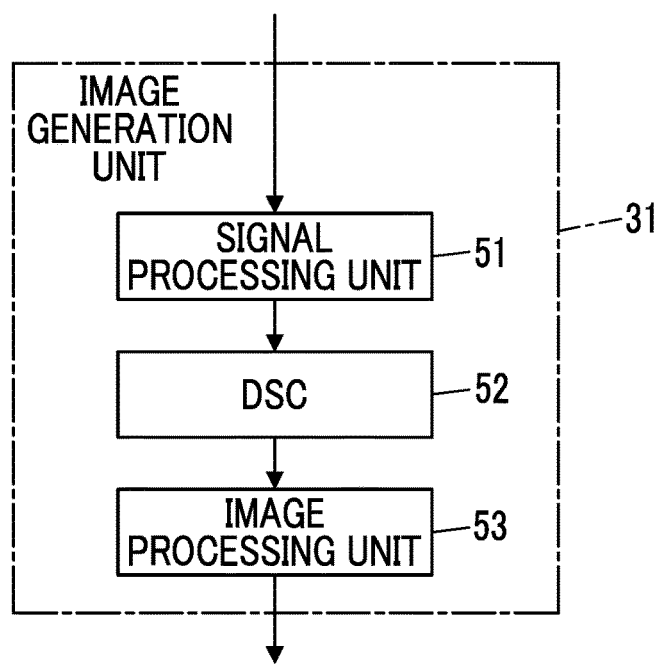
FIG. 3 is a block diagram illustrating an internal configuration of an image generation unit according to the embodiment 1 of the present invention.

As illustrated in FIG. 3, the image generation unit 31 of the apparatus main body 3 has a configuration in which a signal processing unit 51, a digital scan converter (DSC) 52, and an image processing unit 53 are sequentially connected in series.

The signal processing unit 51 performs, on the sound ray signal transmitted from the transmission/reception circuit 22 of the ultrasound probe 2, correction of attenuation due to a distance according to a depth of a reflection position of the ultrasound wave and then performs envelope detection processing. Thereby, an ultrasound image signal (B-mode image signal), which is tomographic image information related to tissues in the subject, is generated.

The DSC 52 converts (raster-converts) the ultrasound image signal generated by the signal processing unit 51 into an image signal conforming to a normal television signal scanning method.

The image processing unit 53 performs various required image processing such as gradation processing on the ultrasound image signal which is input from the DSC 52, and then outputs a signal representing the ultrasound image to the display control unit 32 and the image memory 34. The signal representing the ultrasound image generated by the image generation unit 31 in this way is simply referred to as an ultrasound image.

Under a control of the main body control unit 40, the display control unit 32 performs predetermined processing on the ultrasound image transmitted from the image generation unit 31, and displays the ultrasound image on the monitor 33.

The monitor 33 displays the ultrasound image under a control of the display control unit 32, and includes a display device such as a liquid crystal display (LCD) or an organic electroluminescence (EL) display.

The image memory 34 is a memory that stores the ultrasound image generated by the image generation unit 31 under a control of the main body control unit 40. For example, the image memory 34 can store a plurality of frames of ultrasound images generated by the image generation unit 31 in correspondence with a urinary organ examination of a subject.

As the image memory 34, a flash memory, a hard disc drive (HDD), a solid state drive (SSD), a flexible disc (FD), a magneto-optical (MO) disc, a magnetic tape (MT), a random access memory (RAM), a compact disc (CD), a digital versatile disc (DVD), a secure digital (SD) card, and a recording medium such as a Universal Serial Bus (USB) memory can be used.

The bladder extraction unit 35 extracts a bladder region BR of the subject from the ultrasound image generated by the image generation unit 31. In order to extract the bladder region BR, image recognition can be performed using at least one of template matching, an image analysis technique using feature amounts such as adaptive boosting (Adaboost), support vector machine (SVM), or scale-invariant feature transform (SIFT), or a determination model trained by using a machine learning technique such as deep learning. The determination model is a trained model obtained by learning the bladder region (segmentation) in a learning ultrasound image obtained by imaging the bladder.

The bladder size calculation unit 36 calculates, for example, an area Sp of the bladder region BR as a bladder size representing a size of the bladder region BR in the ultrasound image that is extracted by the bladder extraction unit 35. The bladder size calculation unit 36 can calculate the area Sp of the bladder region BR, for example, by image analysis.

Figure 4:
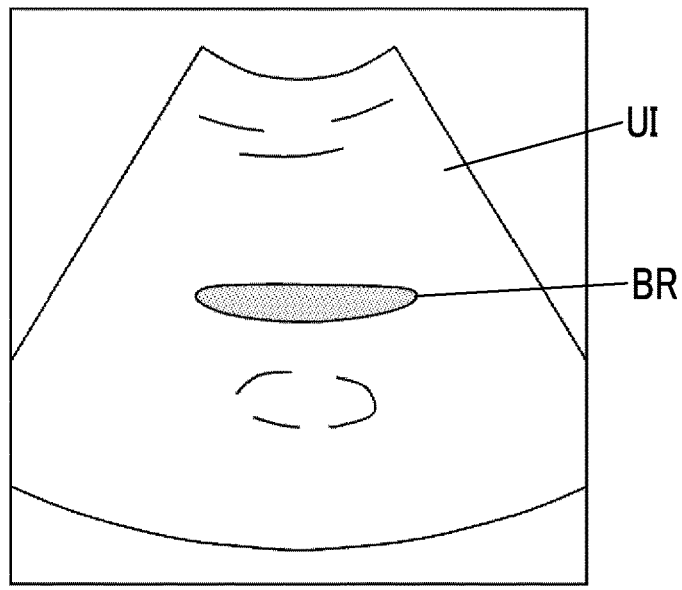
FIG. 4 is a diagram illustrating an ultrasound image in which a bladder region having an area equal to or smaller than a predetermined area threshold value is displayed.

The bladder is a bag-shape organ formed of a flexible and highly elastic mucous membrane, and can store urine therein by expanding and contracting the mucous membrane. In a case where a small amount of urine is stored in the bladder, as illustrated in FIG. 4, the bladder has a flat shape regardless of the gender of the subject, and thus the area Sp of the bladder region BR in the ultrasound image UI decreases. FIG. 4 illustrates a lateral section intersecting with a center line of the subject that extends from a head toward lower limbs of the subject.

On the other hand, as the urine amount in the bladder increases with the passage of time, the bladder expands, and thus the area Sp of the bladder region BR in the ultrasound image increases. At this time, in a case where the subject is a male, since a prostate exists around an urethra downwardly extending from the bladder, a lower portion of the expanded bladder is upwardly pushed by the prostate. Thus, the bladder has a relatively angular shape. On the other hand, in a case where the subject is a female, since a prostate does not exist under the bladder, the expanded bladder has a relatively rounded shape.

Therefore, in order to determine whether or not the bladder is expanded to a certain extent that the gender of the subject can be determined based on the shape of the bladder region BR in the ultrasound image, the bladder size calculation unit 36 calculates the area Sp of the bladder region BR.

In addition, the urine amount in the bladder can be measured based on the area Sp of the bladder region BR that is calculated by the bladder size calculation unit 36. For example, in a case where the bladder is regarded as a rotating ellipsoid, a volume of the bladder can be calculated from the area Sp of the bladder region BR in the ultrasound image UI, and the volume can be converted into the urine amount.

The gender determination unit 37 automatically determines a gender of the subject based on the shape of the bladder region BR that is extracted by the bladder extraction unit 35. In particular, the gender determination unit 37 can determine a gender of the subject based on a curved shape of a lower edge of the bladder region BR.

Here, the gender determination unit 37 compares the size of the bladder region BR that is calculated by the bladder size calculation unit 36 with a predetermined size threshold value, and determines a gender of the subject in a case where the size of the bladder region BR is larger than the size threshold value. In a case where the size of the bladder region BR is equal to or smaller than the size threshold value, the gender determination unit 37 does not determine a gender of the subject. For example, the area Sp of the bladder region BR that is calculated as the size of the bladder region BR by the bladder size calculation unit 36 is compared with an area threshold value Sth as a predetermined size threshold value, and a gender of the subject is determined in a case where the area Sp of the bladder region BR is larger than the area threshold value Sth. In a case where the area Sp of the bladder region BR is equal to or smaller than the area threshold value Sth, a gender of the subject is not determined.

This is because, in a case where the area Sp of the bladder region BR that is calculated by the bladder size calculation unit 36 is equal to or smaller than the predetermined area threshold value Sth, for example, as illustrated in FIG. 4, the bladder has a flat shape regardless of the gender of the subject and reliability of the gender determination of the subject based on the shape of the bladder region BR in the ultrasound image is decreased.

In a case where the area Sp of the bladder region BR is larger than the predetermined area threshold value Sth, the bladder is in a state of being expanded by urine stored therein. At this time, for example, as illustrated by a solid line in FIG. 5, in a case of a bladder region BRm1 of a male, the lower portion of the bladder is upwardly pushed by the prostate, and thus the bladder has a relatively angular shape in the ultrasound image UI. As a result, a curvature radius Rp of a curved portion Cm1 formed at both ends of the lower edge of the bladder region BRm1 decreases. On the other hand, as illustrated by a one-dotted chain line in FIG. 5, in a case of a bladder region BRf1 of a female, the lower portion of the bladder is not upwardly pushed by a prostate, and thus the bladder has a relatively rounded shape in the ultrasound image UI. As a result, a curvature radius Rp of a curved portion Cf1 formed at both ends of the lower edge of the bladder region BRf1 increases.

Figure 5:
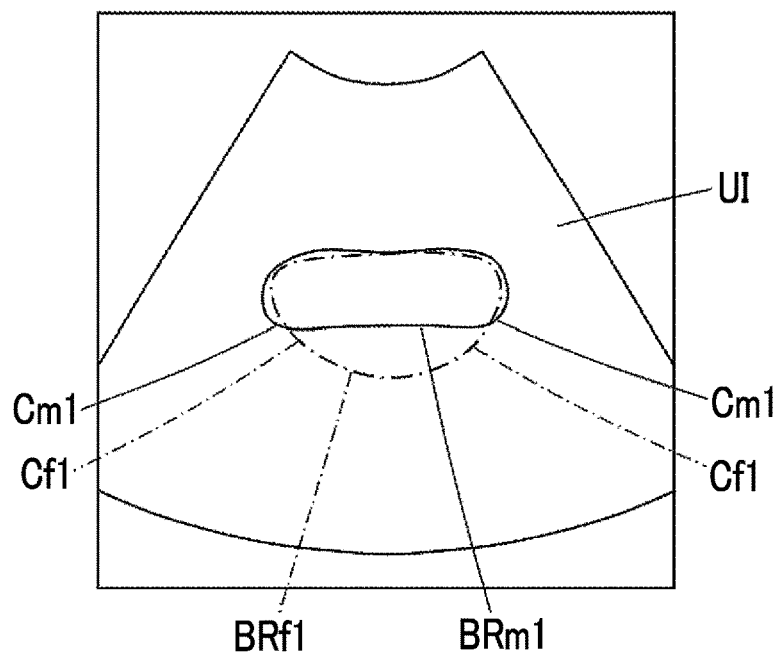
FIG. 5 is a diagram schematically illustrating an example of a bladder region of a male subject and an example of a bladder region of a female subject.

FIG. 5 is a diagram schematically illustrating the bladder region BRm1 of a male and the bladder region BRf1 of a female by being overlapped with each other for convenience in order to compare the shapes, and is different from an actual ultrasound image obtained by imaging a subject.

Therefore, the gender determination unit 37 can determine a gender of the subject by comparing the curvature radius Rp of the curved portion at the both ends of the lower edge of the bladder region BR of the subject that is extracted by the bladder extraction unit 35 with a predetermined curvature radius threshold value Rth. Specifically, the gender determination unit 37 determines that the subject is a male in a case where the curvature radius Rp of the curved portion at the both ends of the lower edge of the bladder region BR of the subject is equal to or smaller than the predetermined curvature radius threshold value Rth, and determines that the subject is a female in a case where the curvature radius Rp of the curved portion at the both ends of the lower edge of the bladder region BR of the subject is larger than the predetermined curvature radius threshold value Rth.

Figure 6:
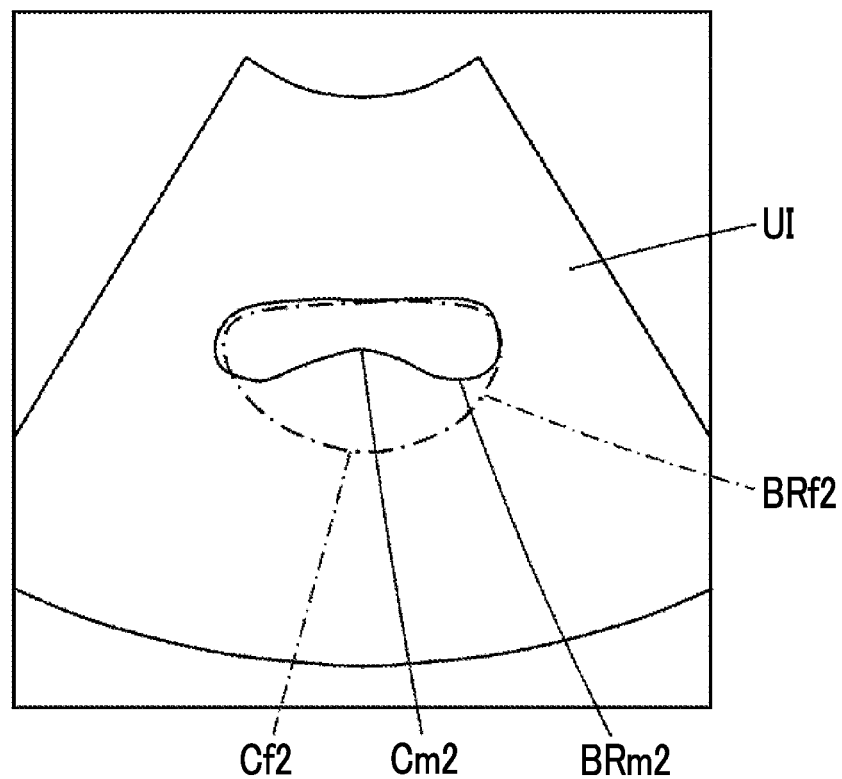
FIG. 6 is a diagram schematically illustrating another example of a bladder region of a male subject and another example of a bladder region of a female subject.

In addition, for example, as illustrated by a solid line in FIG. 6, in a case of a bladder region BRm2 of a male, the lower portion of the bladder is upwardly pushed by the prostate. As a result, at the center of the lower edge of the bladder region BRm2 in the ultrasound image UI, a curved portion Cm2 that is downwardly curved in a recess shape is likely to be formed. On the other hand, as illustrated by a one-dotted chain line in FIG. 6, in a case of a bladder region BRf2 of a female, the lower portion of the bladder is not upwardly pushed by a prostate. As a result, at the center of the lower edge of the bladder region BRf2 in the ultrasound image UI, a curved portion Cf2 that is downwardly curved in a protrusion shape is likely to be formed.

Similar to FIG. 5, FIG. 6 is a diagram schematically illustrating the bladder region BRm2 of a male and the bladder region BRf2 of a female by being overlapped with each other for convenience in order to compare the shapes, and is different from an actual ultrasound image obtained by imaging a subject.

Therefore, the gender determination unit 37 can also determine a gender of the subject by confirming a recess/protrusion of a curve of the curved portion formed at the center of the lower edge of the bladder region BR of the subject that is extracted by the bladder extraction unit 35, that is, by confirming whether the curved portion is downwardly curved in a recess shape or downwardly curved in a protrusion shape. Specifically, the gender determination unit 37 determines that the subject is a male in a case where a curved portion Cm2 which is downwardly curved in a recess shape is formed at the center of the lower edge of the bladder region BR of the subject, and determines that the subject is a female in a case where a curved portion Cf2 which is downwardly curved in a protrusion shape is formed at the center of the lower edge of the bladder region BR of the subject.

In addition, the gender determination unit 37 can also determine a gender of the subject by using a machine learning technique such as deep learning. For example, the gender determination unit 37 can determine a gender of the subject by using a trained determination model obtained by learning shapes of bladder regions in ultrasound images obtained by imaging a bladder of a male and ultrasound images obtained by imaging a bladder of a female.

The observation support unit 38 supports an observation of a next observation site which is determined according to the gender of the subject determined by the gender determination unit 37.

Usually, in a urinary organ examination, in a case of a male subject, a prostate is measured next to a bladder, and in a case of a female subject, a uterus is measured next to a bladder. That is, in a case where the subject is a male, a prostate is determined as a next observation site next to the bladder, and in a case where the subject is a female, a uterus is determined as a next observation site next to the bladder.

Therefore, in a case where the gender determination unit 37 determines that the subject is a male, the observation support unit 38 notifies a user that the next observation site is a prostate, and in a case where the gender determination unit 37 determines that the subject is a female, the observation support unit 38 notifies a user that the next observation site is a uterus. As a method of notifying the user of the next observation site, the notification content may be displayed on the monitor 33, or in a case where the apparatus main body 3 includes a speaker (not illustrated), the notification content may be provided by voice via the speaker.

In addition, the observation support unit 38 may guide the user to operate the ultrasound probe 2 such that the next observation site is visualized on the monitor 33, in addition to the notification of the next observation site. For example, in a case where the gender determination unit 37 determines that the subject is a male, the observation support unit 38 can guide the user to move the ultrasound probe 2 in parallel while maintaining a lateral section or to tilt the ultrasound probe 2 such that a prostate as the next observation site can be seen to be large. In a case where the gender determination unit 37 determines that the subject is a female, the observation support unit 38 can guide the user to switch the ultrasound probe 2 from a lateral section to a longitudinal section by rotating the ultrasound probe 2 by 90 degrees such that a uterus as the next observation site can be seen to be large.

Further, the observation support unit 38 can also automatically recognize the next observation site from the ultrasound image generated by the image generation unit 31. That is, instead of notifying the user that the next observation site is a prostate or a uterus or guiding the user to operate the ultrasound probe 2 such that the next observation site is visualized on the monitor 33, the observation support unit 38 may automatically recognize a prostate or a uterus as the next observation site by analyzing the ultrasound image.

The main body control unit 40 controls each unit of the apparatus main body 3 and the transmission/reception circuit 22 of the ultrasound probe 2 based on a control program or the like which is stored in advance.

In addition, a main-body-side storage unit (not illustrated) is connected to the main body control unit 40. The main-body-side storage unit stores a control program or the like. In addition, as the main-body-side storage unit, for example, a flash memory, a RAM, an SD card, an SSD, or the like can be used.

The input device 41 is a device that allows a user to perform an input operation, and includes, for example, devices such as a keyboard, a mouse, a trackball, a touch pad, and a touch sensor overlapped and provided on the monitor 33.

Note that the processor 42 including the image generation unit 31, the display control unit 32, the bladder extraction unit 35, the bladder size calculation unit 36, the gender determination unit 37, the observation support unit 38, and the main body control unit 40 is configured with a central processing unit (CPU) and a control program for causing the CPU to perform various processing. The processor 42 may be configured by using a field programmable gate array (FPGA), a digital signal processor (DSP), an application specific integrated circuit (ASIC), a graphics processing unit (GPU), or other integrated circuits (IC), or may be configured by using a combination thereof.

In addition, the image generation unit 31, the display control unit 32, the bladder extraction unit 35, the bladder size calculation unit 36, the gender determination unit 37, the observation support unit 38, and the main body control unit 40 of the processor 42 can be partially or entirely integrated into one CPU or the like.

Figure 7:
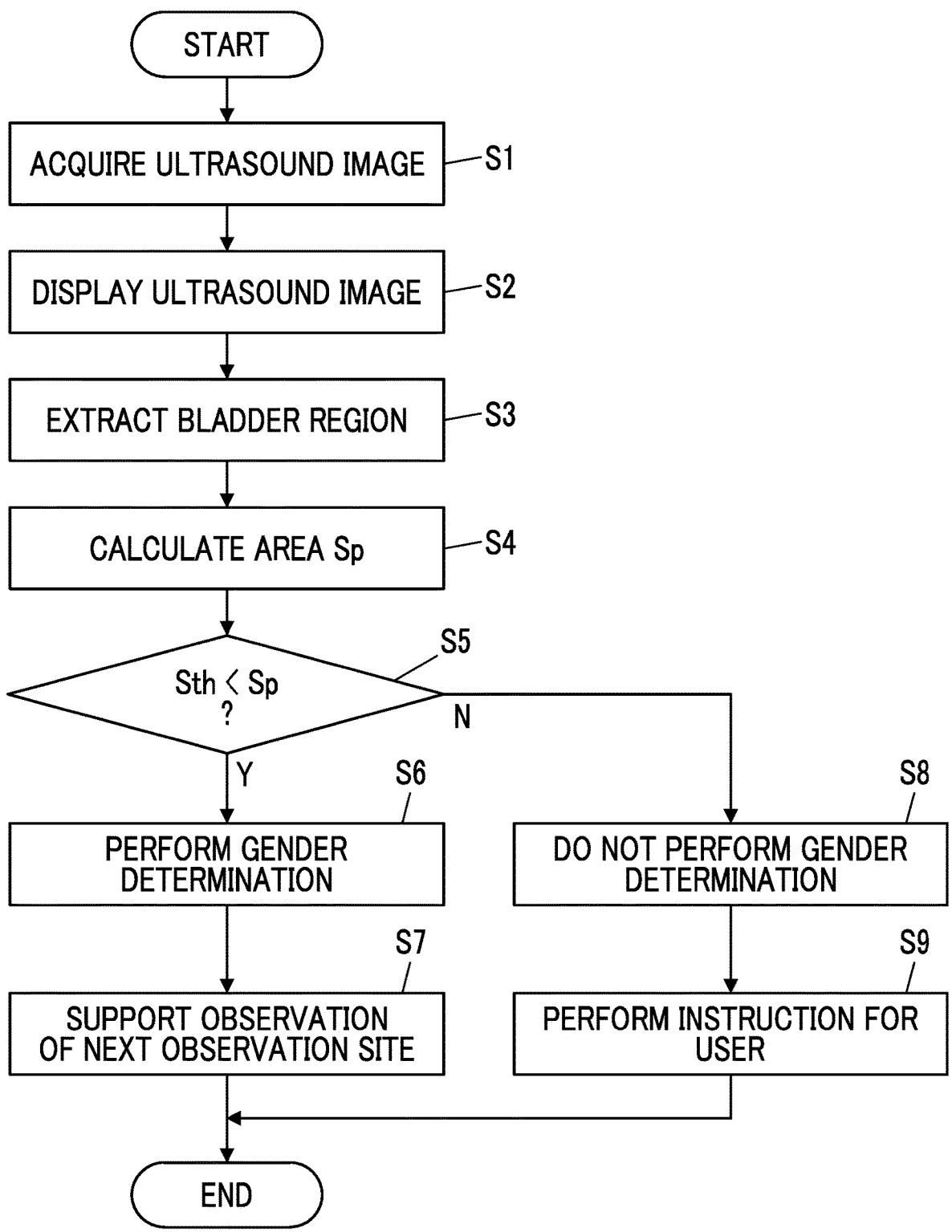
FIG. 7 is a flowchart illustrating an operation of the ultrasound diagnostic apparatus according to the embodiment 1.

Next, an operation of the ultrasound diagnostic apparatus 1 according to the embodiment 1 will be described with reference to a flowchart illustrated in FIG. 7.

Prior to a urinary organ examination, the user inputs subject information such as an identifier (ID, identification information) of the subject as an examination target via the input device 41.

In step S1, a lower abdomen of a subject is imaged by using the ultrasound probe 2, and thus an ultrasound image is acquired. At this time, under a control of the main body control unit 40, transmission and reception of ultrasound waves from the plurality of transducers of the transducer array 21 are started according to a drive signal from the pulser 23 of the transmission/reception circuit 22 of the ultrasound probe 2. The ultrasound echo from the inside of the bladder of the subject is received by the plurality of transducers of the transducer array 21. The reception signal which is an analog signal is output to the amplification unit 24, and is amplified by the amplification unit 24. The amplified reception signal is AD-converted by the AD conversion unit 25, and thus the reception data is acquired.

The reception focus processing is performed on the reception data by the beam former 26, and the sound ray signal generated by the reception focus processing is transmitted to the image generation unit 31 of the apparatus main body 3. An ultrasound image representing lateral-section image information of the lower abdomen of the subject is generated by the image generation unit 31. At this time, attenuation correction according to a depth of a reflection position of the ultrasound wave and envelope detection processing are performed on the sound ray signal by the signal processing unit 51 of the image generation unit 31. The sound ray signal is converted into an image signal conforming to a scanning method of a normal television signal by the DSC 52, and various required image processing such as gradation processing is performed on the image signal by the image processing unit 53.

Subsequently, in step S2, the ultrasound image generated by the image generation unit 31 is displayed on the monitor 33 via the display control unit 32, and is stored in the image memory 34.

In the acquisition of the ultrasound image, it is assumed that a transmission intensity of the ultrasound wave and a depth range of the ultrasound image displayed on the monitor 33 are adjusted under a control of the main body control unit 40 such that at least the entire bladder of the subject is included in the screen.

In a case where the ultrasound image is stored in the image memory 34 in this way, in step S3, the ultrasound image is input to the bladder extraction unit 35, and a bladder region BR of the subject is extracted from the ultrasound image by the bladder extraction unit 35. The extraction of the bladder region BR by the bladder extraction unit 35 is performed by image analysis or by using deep learning.

In a case where the bladder region BR is extracted from the ultrasound image by the bladder extraction unit 35, in step S4, an area Sp of the bladder region BR in the ultrasound image is calculated by the bladder size calculation unit 36.

Further, a urine amount in the bladder can be measured based on the area Sp of the bladder region BR that is calculated by the bladder size calculation unit 36.

The ultrasound image and the area Sp of the bladder region BR that is calculated by the bladder size calculation unit 36 are input to the gender determination unit 37. In step S5, a comparison of the area Sp of the bladder region BR with a predetermined area threshold value Sth is performed by the gender determination unit 37.

As a result of the comparison, in a case where the area Sp of the bladder region BR that is calculated by the bladder size calculation unit 36 is larger than the predetermined area threshold value Sth, it is determined that a gender of the subject can be determined based on a shape of the bladder region BR. In this case, the process proceeds to step S6, and a gender of the subject is automatically determined by the gender determination unit 37.

For example, the gender determination unit 37 calculates a curvature radius Rp of a curved portion at both ends of the lower edge of the bladder region BR, and compares the calculated curvature radius Rp with a predetermined curvature radius threshold value Rth. In a case where the curvature radius Rp is equal to or smaller than the predetermined curvature radius threshold value Rth, it is determined that the subject is a male. In a case where the curvature radius Rp is larger than the predetermined curvature radius threshold value Rth, it is determined that the subject is a female.

Alternatively, the gender determination unit 37 can confirm a recess/protrusion of a curve of the curved portion formed at the center of the lower edge of the bladder region BR, determine that the subject is a male in a case where a curved portion which is downwardly curved in a recess shape is formed at the center of the lower edge of the bladder region BR, and determine that the subject is a female in a case where a curved portion which is downwardly curved in a protrusion shape is formed at the center of the lower edge of the bladder region BR.

In addition, the gender determination unit 37 may determine a gender of the subject by using a trained determination model obtained by learning shapes of bladder regions in ultrasound images obtained by imaging a bladder of a male and ultrasound images obtained by imaging a bladder of a female.

In this way, in a case where the gender of the subject is determined by the gender determination unit 37, in step S7, the observation support unit 38 supports, for the user, an observation of the next observation site that is determined according to the gender of the subject.

Figure 8:
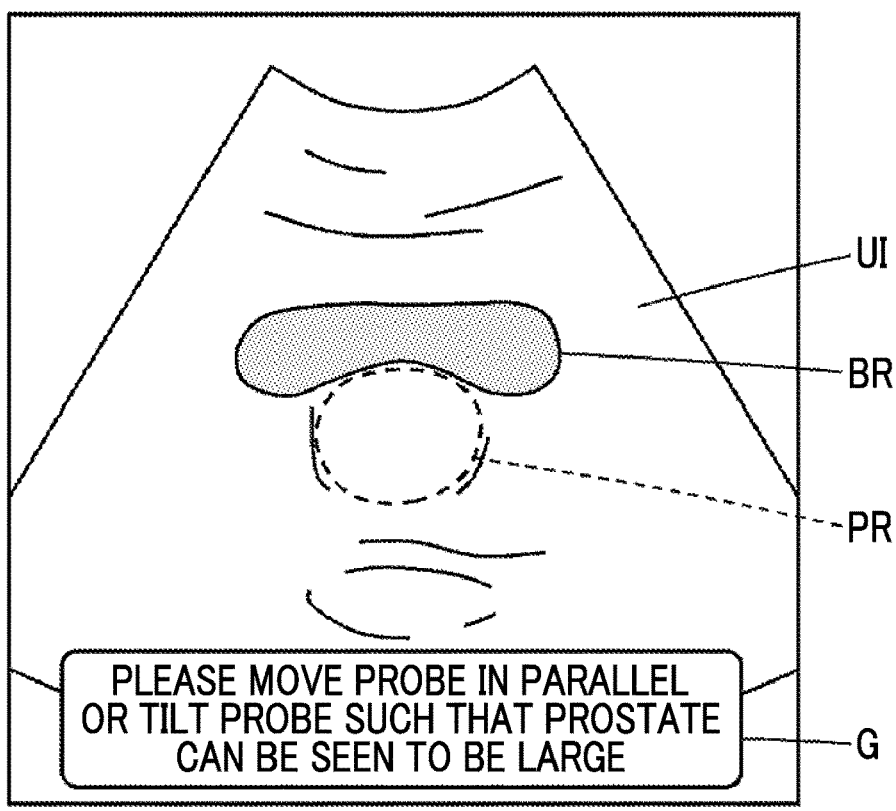
FIG. 8 is a diagram schematically illustrating an ultrasound image in which a bladder region of a male subject is displayed.

For example, as illustrated in FIG. 8, in a case where it is determined that the subject is a male based on the shape of the bladder region BR in the ultrasound image UI, the prostate is determined as the next observation site, and a notification related to an observation of the prostate is performed by the observation support unit 38. FIG. 8 illustrates a lateral section intersecting with a center line of the subject that extends from a head toward lower limbs of the subject. Specifically, the observation support unit 38 can display a message "The next observation site is the prostate" on the monitor 33 via the display control unit 32.

Here, it is desirable that the observation support unit 38 not only notifies the user of the next observation site but also guide the user to operate the ultrasound probe 2 such that the prostate as the next observation site is visualized on the monitor 33. For example, as illustrated in FIG. 8, a guide message G "Please move the probe in parallel or tilt the probe such that the prostate can be seen to be large" is displayed. That is, the user is guided to move the ultrasound probe 2 while maintaining the lateral section such that the prostate is clearly and largely visualized on the monitor 33. The guide message G may be displayed on the monitor 33 at a position by being overlapped on the ultrasound image UI, or may be displayed outside the ultrasound image UI.

Figure 9:
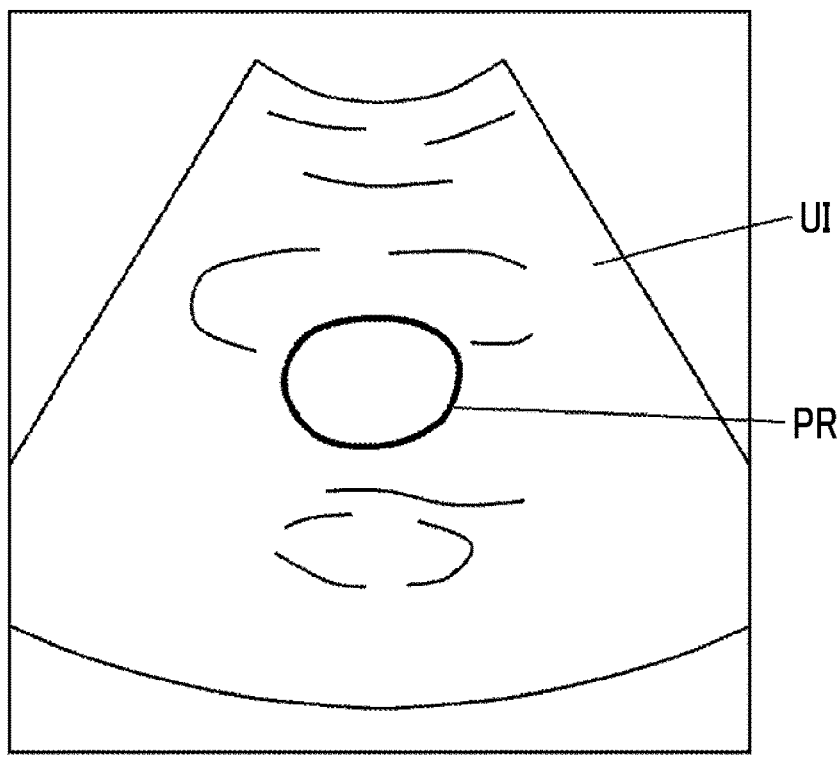
FIG. 9 is a diagram schematically illustrating an ultrasound image in which a prostate is displayed.

By operating the ultrasound probe 2 according to the guide message G, as illustrated in FIG. 9, the prostate PR as the next observation site can be visualized in the ultrasound image UI.

Figure 10:
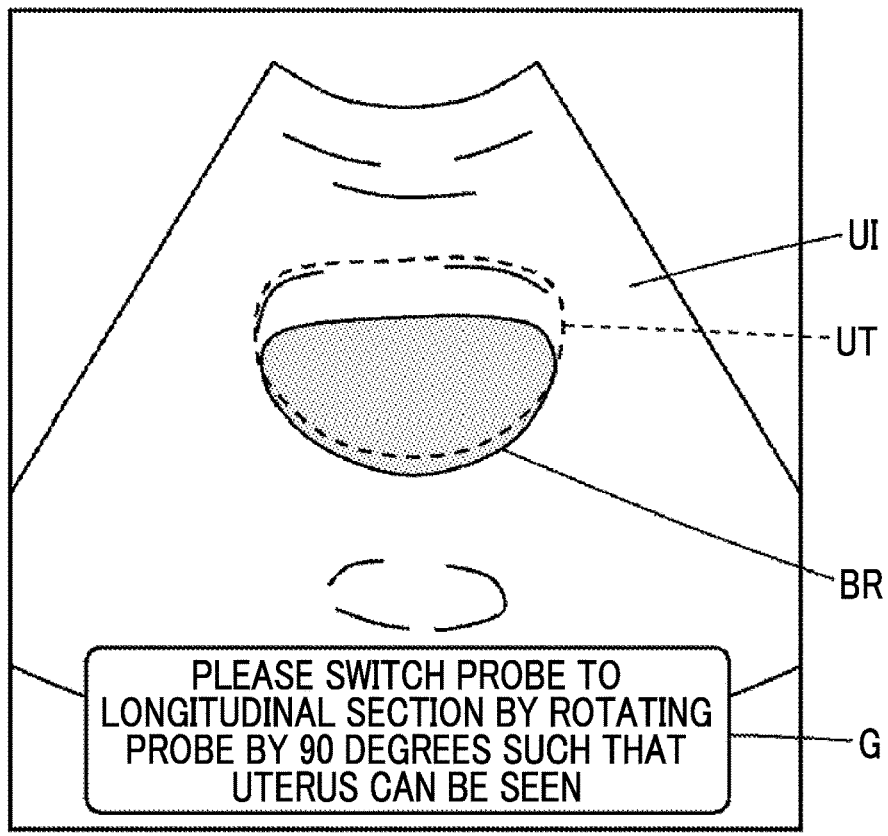
FIG. 10 is a diagram schematically illustrating an ultrasound image in which a bladder region of a female subject is displayed.

In addition, for example, as illustrated in FIG. 10, in a case where it is determined that the subject is a female based on the shape of the bladder region BR in the ultrasound image UI, the uterus is determined as the next observation site, and a notification related to an observation of the uterus is performed by the observation support unit 38. FIG. 10 illustrates a lateral section intersecting with a center line of the subject that extends from a head toward lower limbs of the subject. In the ultrasound image UI, a part of the uterus UT is overlapped with the bladder region BR. As a result, the section may not be suitable for the observation of the uterus UT.

Specifically, the observation support unit 38 can display a message "The next observation site is the uterus" on the monitor 33 via the display control unit 32.

Here, it is desirable that the observation support unit 38 not only notifies the user of the next observation site but also guide the user to operate the ultrasound probe 2 such that the uterus as the next observation site is visualized on the monitor 33. For example, as illustrated in FIG. 10, a guide message G "Please switch the probe to a longitudinal section by rotating the probe by 90 degrees such that the uterus can be seen to be large" is displayed. That is, the user is guided to switch the ultrasound probe 2 from a lateral section to a longitudinal section by rotating a direction of the ultrasound probe 2 when imaging the ultrasound image UI of FIG. 10 by 90 degrees such that the uterus is clearly visualized on the monitor 33.

Figure 11:
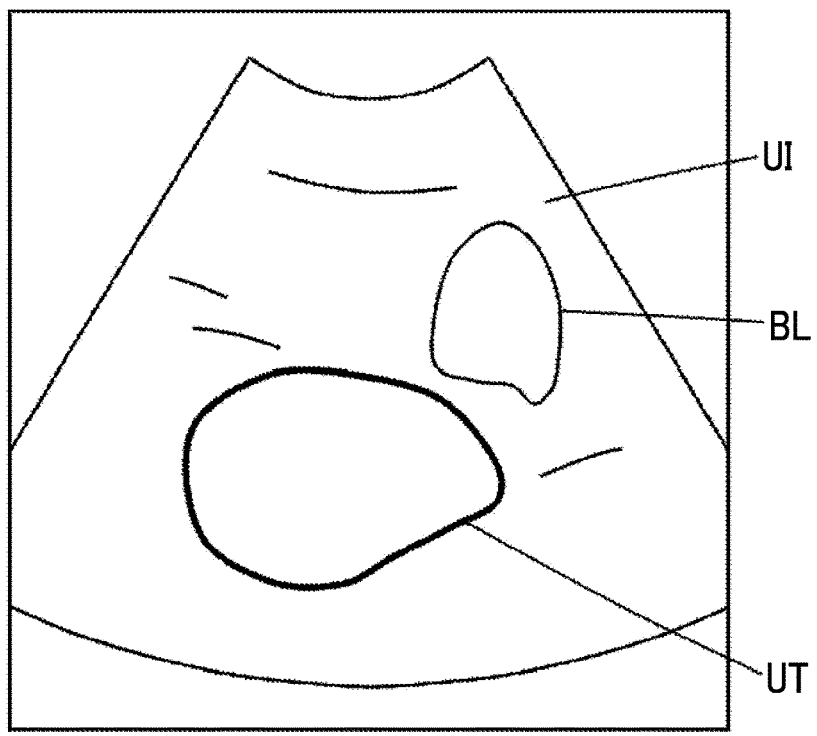
FIG. 11 is a diagram schematically illustrating an ultrasound image in which a uterus is displayed.

By operating the ultrasound probe 2 according to the guide message G, as illustrated in FIG. 11, the uterus UT as the next observation site can be clearly visualized in the ultrasound image UI without being overlapped with the bladder BL.

The support for the observation of the next observation site in step S7 is not limited to the notification of the next observation site and the guide for the operation of the ultrasound probe 2. The observation support unit 38 can automatically recognize the prostate PR or the uterus UT as the next observation site from the ultrasound image UI, and display the prostate PR or the uterus UT on the monitor 33. The next observation site that is automatically recognized by the observation support unit 38 may be highlight-displayed on the monitor 33 or may be displayed on the monitor 33 by being enlarged.

As a result of the comparison in step S5, in a case where it is determined that the area Sp of the bladder region BR that is calculated by the bladder size calculation unit 36 is equal to or smaller than the predetermined area threshold value Sth, it is determined that it is difficult to perform reliable gender determination based on the shape of the bladder region BR. In this case, the process proceeds to step S8, and automatic gender determination is not performed by the gender determination unit 37. Therefore, the observation support unit 38 notifies the user that gender determination of the subject is not performed.

Further, in step S9, the observation support unit 38 instructs the user to perform examination such that gender determination by the gender determination unit 37 can be performed.

For example, the observation support unit 38 can instruct the user to perform re-examination after a lapse of a predetermined time.

As illustrated in FIG. 4, in a case where a small amount of urine is stored in the bladder and thus the area Sp of the bladder region BR is equal to or smaller than the area threshold value Sth, the urine amount in the bladder increases with the passage of time. Thus, in a case where re-examination is performed after a lapse of a predetermined time, the area Sp of the bladder region BR is larger than the area threshold value Sth. Therefore, gender determination of the subject may be performed by the gender determination unit 37.

A rate at which urine is accumulated in the bladder varies depending on the individual subject. On the other hand, by using a value of an average rate, the observation support unit 38 can display, for example, a message "The urine amount is smaller than a specified amount by X milliliters. Please perform re-examination after Y hours." on the monitor 33 via the display control unit 32.

In addition, in step S9, the observation support unit 38 can also instruct the user to perform re-examination after an input of information related to the gender of the subject to the apparatus main body 3 via the input device 41. For example, the observation support unit 38 displays a message "The gender determination cannot be performed because the urine amount is small. Please input gender information." on the monitor 33 via the display control unit 32.

In this case, in the re-examination, the gender determination unit 37 does not compare the area Sp of the bladder region BR in the ultrasound image UI with the predetermined area threshold value Sth, and the observation support unit 38 notifies the user of the next observation site that is determined according to the information related to the gender of the subject, the information being input via the input device 41.

Further, in step S9, the observation support unit 38 can instruct the user to move the ultrasound probe 2 and find a section in which the area Sp of the bladder region BR extracted by the bladder extraction unit 35 and displayed on the monitor 33 is increased.

In a case where the ultrasound image UI acquired in step S1 is not an image having a section suitable for gender determination and the bladder region BR is imaged as being smaller than the actual bladder, by moving the ultrasound probe 2 and imaging an ultrasound image UI again, an ultrasound image UI having a section in which the area Sp of the bladder region BR is increased may be acquired. In a case where an ultrasound image UI is imaged again and the area Sp of the bladder region BR is larger than the predetermined area threshold value Sth, the gender determination unit 37 can determine the gender, and the observation support unit 38 can notify the user of an observation of the next observation site that is determined according to the gender of the subject.

Further, assuming that the gender of the subject is included in subject information which is input prior to the urinary organ examination, in a case where a result of the gender determination that is performed based on the shape of the bladder region BR of the subject by the gender determination unit 37 in step S6 is different from the gender of the subject included in the subject information, it is desirable that the observation support unit 38 notifies the user of the fact.

Even in a case where the gender of the subject is not included in the subject information which is input but the gender can be inferred from a name of the subject, when a result of the gender determination in step S6 is different from the gender inferred from the name of the subject, it is desirable that the observation support unit 38 notifies the user of the fact.

Further, the gender determination unit 37 can be configured to perform automatic gender determination only in a case where the gender of the subject cannot be determined from the subject information which is input prior to the urinary organ examination.

As described above, according to the ultrasound diagnostic apparatus 1 of the embodiment 1, the bladder region BR is extracted from the ultrasound image UI by the bladder extraction unit 35, the gender of the subject is determined based on the shape of the bladder region BR by the gender determination unit 37 in a case where the area Sp of the bladder region BR that is calculated by the bladder size calculation unit 36 is larger than the area threshold value Sth, and the observation support unit 38 supports an observation of the next observation site that is determined according to the gender of the subject. Therefore, it is possible to perform an appropriate examination corresponding to the gender of the subject without requiring the user to input the gender of the subject.

In the embodiment 1, the bladder size calculation unit 36 calculates, as the bladder size, the area Sp of the bladder region BR extracted by the bladder extraction unit 35, and the gender determination unit 37 determines whether or not gender determination can be performed based on the shape of the bladder region BR. On the other hand, the bladder size calculation unit 36 can also calculate, as the bladder size, a contour length of the bladder region BR or a major axis length and a minor axis length of the bladder region BR, instead of the area Sp of the bladder region BR. In this case, the gender determination unit 37 performs gender determination in a case where the contour length of the bladder region BR that is calculated by the bladder size calculation unit 36 is longer than a contour length threshold value which is set as a size threshold value, or in a case where the bladder sizes including the major axis length and the minor axis length of the bladder region BR are larger than a major axis length threshold value and a minor axis length threshold value which are set as size threshold values. In a case where the calculated bladder size is equal to or smaller than the threshold value, gender determination is not performed.

In addition, the reason why the bladder size calculation unit 36 calculates the bladder size is to determine whether or not the gender determination unit 37 can perform gender determination based on the shape of the bladder region BR. Thus, it is not always necessary to calculate the size of the bladder region BR itself. A configuration in which at least a size of a region including the bladder region BR is calculated as the bladder size and the gender determination unit 37 determines whether to perform gender determination based on the calculated bladder size can be adopted.

That is, in the embodiment 1, the bladder extraction unit 35 extracts the bladder region BR from the ultrasound image, and the bladder size calculation unit 36 calculates the bladder size of the extracted bladder region BR. On the other hand, the present invention is not limited thereto. The bladder extraction unit 35 may extract a first region including the bladder region BR from the ultrasound image, and the bladder size calculation unit 36 may calculate, as the bladder size, a size of the extracted first region.

The first region is a region including at least the bladder region BR. As in the embodiment 1, the bladder extraction unit 35 may extract the bladder region BR itself as the first region. Alternatively, the bladder extraction unit 35 can also extract, as the first region, any one of a region surrounded by a circumscribing rectangle that circumscribes the bladder region BR, a region surrounded by a circumscribing ellipse that circumscribes the bladder region BR, a region surrounded by a rectangle including a circumscribing rectangle that circumscribes the bladder region BR, and a region surrounded by an ellipse including a circumscribing ellipse that circumscribes the bladder region BR.

Further, the bladder extraction unit 35 may extract, as the first region, a region surrounded by a circumscribing circle that circumscribes the bladder region BR or a region surrounded by a circle including a circumscribing circle that circumscribes the bladder region BR.

The "circumscribing rectangle" means a rectangle which includes the bladder region BR and of which four sides are in contact with the bladder region BR. The "rectangle including a circumscribing rectangle" means a rectangle of which four sides are located outside the circumscribing rectangle and which is an outer rectangle in which the included circumscribing rectangle has an occupancy rate of 80% to 90%. Such an outer rectangle can be obtained by enlarging a long side (lateral side) and a short side (longitudinal side) of the circumscribing rectangle by the same magnification or different magnifications.

In addition, the "circumscribing ellipse" means an ellipse which includes the bladder region BR and in which the bladder region BR has an occupancy rate of 80% to 90%. The "ellipse including the circumscribing ellipse" means an outer ellipse in which the included circumscribing ellipse has an occupancy rate of 80% to 90%. Such an outer ellipse can be obtained by enlarging a major axis (lateral axis) and a minor axis (longitudinal axis) of the circumscribing ellipse by the same magnification or different magnifications.

Further, the "circumscribing circle" means a perfect circle that includes the bladder region BR and is a circle of which the diameter is a lateral width of the bladder region BR (a dimension of a width perpendicular to a body length direction of the subject). The "circle including the circumscribing circle" means an outer circle in which the included circumscribing circle has an occupancy rate of 80% to 90%.

In a case where the bladder extraction unit 35 extracts, as the first region, a region surrounded by the circumscribing rectangle that circumscribes the bladder region BR, the bladder size calculation unit 36 can calculate, as the bladder size, any one of an area, a circumference length (a total length of four sides of the circumscribing rectangle), and a length of a longitudinal side (side along a body length direction of the subject) of the circumscribing rectangle of the extracted first region. The reason why the bladder size calculation unit 36 calculates the length of the longitudinal side of the circumscribing rectangle is that the bladder extends in a longitudinal direction (a body length direction of the subject) as the urine amount in the bladder increases.

In addition, in a case where the bladder extraction unit 35 extracts, as the first region, a region surrounded by the circumscribing ellipse that circumscribes the bladder region BR, the bladder size calculation unit 36 can calculate, as the bladder size, any one of an area, a circumference length, a minor axis (a longitudinal diameter), a major axis (a lateral diameter), and a flat ratio (a ratio of the minor axis to the major axis) of the circumscribing ellipse of the extracted first region. The reason why the bladder size calculation unit 36 calculates the flat ratio of the circumscribing ellipse is that the bladder extends in a longitudinal direction (a body length direction of the subject) and thus the flat ratio of the circumscribing ellipse changes as the urine amount in the bladder increases.

Further, in a case where the bladder extraction unit 35 extracts, as the first region, a region surrounded by the circumscribing circle that circumscribes the bladder region BR, the bladder size calculation unit 36 can calculate, as the bladder size, any one of an area, a circumference length, a radius, and a diameter of the circumscribing circle of the extracted first region. In particular, in a case where a lateral width of the bladder changes according to the urine amount in the bladder, the calculation of the bladder size using the circumscribing circle is effective.

In a case where the bladder extraction unit 35 extracts, as the first region, a region surrounded by a rectangle including the circumscribing rectangle that circumscribes the bladder region BR, the bladder size calculation unit 36 can calculate, as the bladder size, any one of an area, a circumference length (a total length of four sides of the rectangle), and a length of a longitudinal side (side along a body length direction of the subject) of the rectangle including the circumscribing rectangle.

In addition, in a case where the bladder extraction unit 35 extracts, as the first region, a region surrounded by an ellipse including the circumscribing ellipse that circumscribes the bladder region BR, the bladder size calculation unit 36 can calculate, as the bladder size, any one of an area, a circumference length, a minor axis (a longitudinal diameter), a major axis (a lateral diameter), and a flat ratio (a ratio of the minor axis to the major axis) of the ellipse including the circumscribing ellipse.

Further, in a case where the bladder extraction unit 35 extracts, as the first region, a region surrounded by a circle including the circumscribing circle that circumscribes the bladder region BR, the bladder size calculation unit 36 can calculate, as the bladder size, any one of an area, a circumference length, a radius, and a diameter of the circle including the circumscribing circle.

In this way, even in a case where the bladder extraction unit 35 extracts the first region including the bladder region BR from the ultrasound image and the bladder size calculation unit 36 calculates, as the bladder size, the size of the extracted first region, the gender determination unit 37 compares the bladder size calculated by the bladder size calculation unit 36 with the predetermined size threshold value. In a case where the bladder size is larger than the size threshold value, the gender determination unit 37 determines that the gender of the subject can be determined based on the shape of the bladder region BR, and automatically performs gender determination. In a case where the bladder size is equal to or smaller than the size threshold value, the gender determination unit 37 determines that it is difficult to perform reliable gender determination based on the shape of the bladder region BR, and does not perform gender determination.

Embodiment 2

Figure 12:
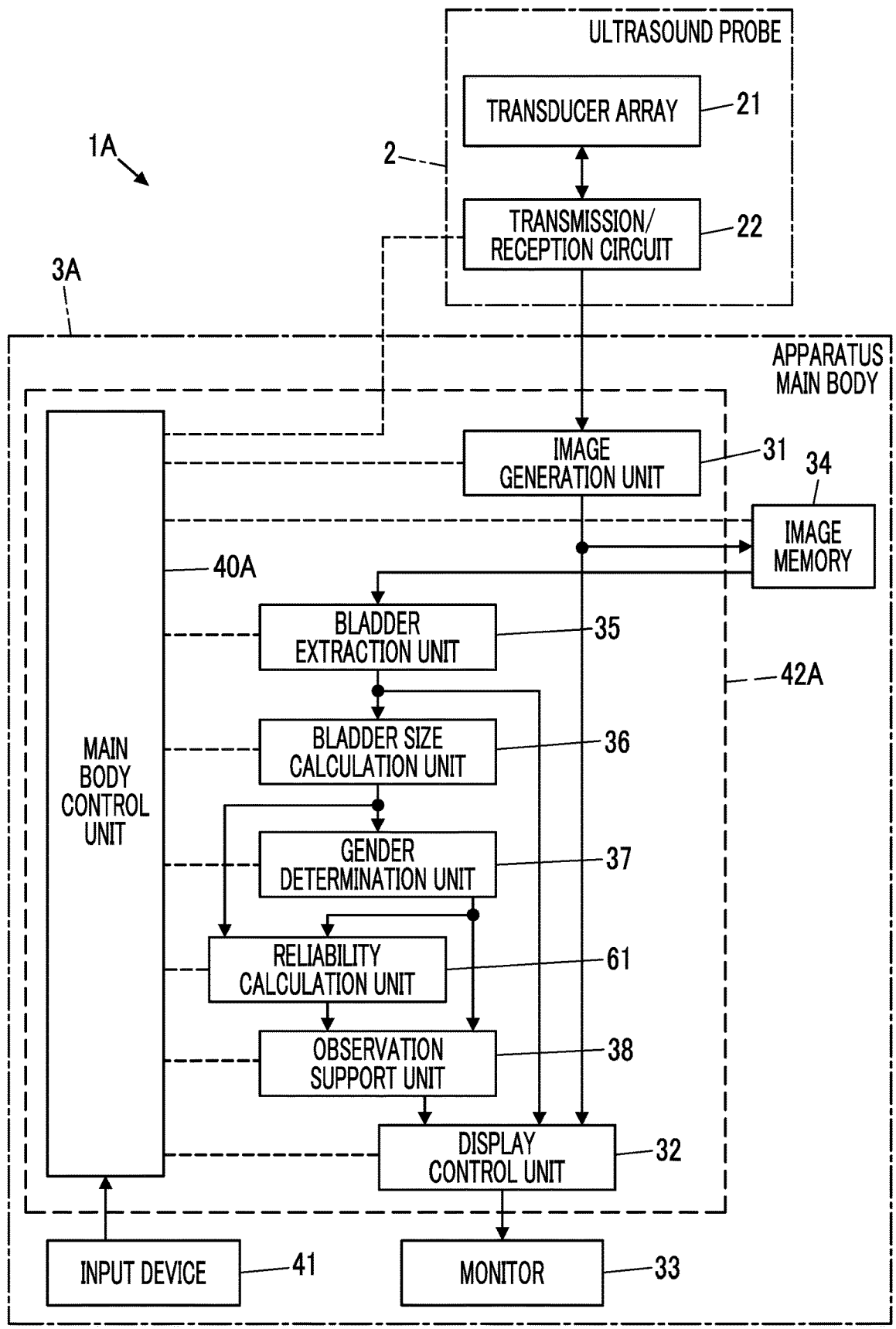
FIG. 12 is a block diagram illustrating a configuration of an ultrasound diagnostic apparatus according to an embodiment 2.

FIG. 12 illustrates a configuration of an ultrasound diagnostic apparatus 1A according to an embodiment 2. In the ultrasound diagnostic apparatus 1A, an ultrasound probe 2 is connected to an apparatus main body 3A. The apparatus main body 3A is obtained by newly adding a reliability calculation unit 61 to the apparatus main body 3 of the ultrasound diagnostic apparatus 1 according to the embodiment 1 illustrated in FIG. 1 and using a main body control unit 40A instead of the main body control unit 40. Other configurations are the same as those of the apparatus main body 3 according to the embodiment 1.

In the ultrasound diagnostic apparatus 1A according to the embodiment 2, the gender determination unit 37 is configured to calculate a reliability of the gender determination of the subject and notify the user of the reliability.

The reliability calculation unit 61 is connected to the bladder size calculation unit 36 and the gender determination unit 37, and the observation support unit 38 is connected to the reliability calculation unit 61.

A main body control unit 40A is connected to the image generation unit 31, the display control unit 32, the image memory 34, the bladder extraction unit 35, the bladder size calculation unit 36, the gender determination unit 37, the observation support unit 38, and the reliability calculation unit 61. An input device 41 is connected to the main body control unit 40A.

A processor 42A is configured by the image generation unit 31, the display control unit 32, the bladder extraction unit 35, the bladder size calculation unit 36, the gender determination unit 37, the observation support unit 38, the main body control unit 40A, and the reliability calculation unit 61.

The reliability calculation unit 61 calculates a reliability of gender determination of the subject in the gender determination unit 37. As the urine amount stored in the bladder increases, the bladder expands. In the ultrasound image, it is assumed that the bladder region BR of a male is upwardly pushed by the prostate and thus has a relatively angular shape and that the bladder region BR of a female has an increasingly rounded shape. That is, a difference in the shape of the bladder region BR between the genders becomes larger according to the area Sp of the bladder region BR in the ultrasound image. Thus, a reliability of the gender determination based on the shape of the bladder region BR in the gender determination unit 37 is improved.

In addition, in the gender determination in the gender determination unit 37, the reliability of the gender determination is also influenced by the curvature radius Rp of the curved portion at both ends of the lower edge of the bladder region BR of the subject as a determination target and a recess/protrusion of a curve of the curved portion formed at the center of the lower edge of the bladder region BR.

Further, as the ultrasound image to be used for the determination in the gender determination unit 37 has a higher image quality in contrast, sharpness, and the like, the reliability of the gender determination is increased. As the ultrasound image has a lower image quality, the reliability of the gender determination is decreased.

Therefore, in a case where the area Sp of the bladder region BR that is calculated by the bladder size calculation unit 36, the curvature radius Rp of the curved portion at both ends of the lower edge of the bladder region BR that is calculated by the gender determination unit 37, the recess/protrusion of the curve of the curved portion formed at the center of the lower edge of the bladder region BR that is confirmed by the gender determination unit 37, and the image quality of the ultrasound image that is used for the determination in the gender determination unit 37 are input as input information, the reliability calculation unit 61 calculates a reliability of the gender determination in the gender determination unit 37 based on the input information.

The reliability of the gender determination that is calculated by the reliability calculation unit 61 is transmitted to the observation support unit 38, and the observation support unit 38 displays the reliability of the gender determination on the monitor 33 via the display control unit 32. The reliability of the gender determination may be displayed on the monitor 33 by a numerical value, or may be displayed on the monitor 33 by a pie graph, a bar graph, or the like.

By confirming the reliability of the gender determination that is displayed on the monitor 33, the user can accurately perform an observation of the prostate or the uterus as the next observation site of the bladder in a series of urinary organ examination.

The method of connecting the ultrasound probe 2 and the apparatus main body 3 or 3A in the embodiments 1 and 2 is not particularly limited, and a wired connection method or a wireless connection method may be used.

In the embodiments 1 and 2, the ultrasound probe 2 includes the transmission/reception circuit 22. On the other hand, the apparatus main body 3 or 3A may include the transmission/reception circuit 22. In addition, the apparatus main body 3 or 3A includes the image generation unit 31. On the other hand, the ultrasound probe 2 may include the image generation unit 31. Further, the image generation unit 31 illustrated in FIG. 3 includes the signal processing unit 51, the DSC 52, and the image processing unit 53. On the other hand, the ultrasound probe 2 may include only the signal processing unit 51, and the apparatus main body 3 or 3A may include the DSC 52 and the image processing unit 53.

In addition, in the embodiments 1 and 2, as the apparatus main body 3 or 3A, a portable or handheld compact apparatus main body can be used, and a stationary apparatus main body can also be used.

Embodiment 3

The ultrasound diagnostic apparatus 1 according to the embodiment 1 has a configuration in which the ultrasound probe 2, the monitor 33, and the input device 41 are directly connected to the processor 42 of the apparatus main body 3. On the other hand, the present invention is not limited thereto.

Figure 13:
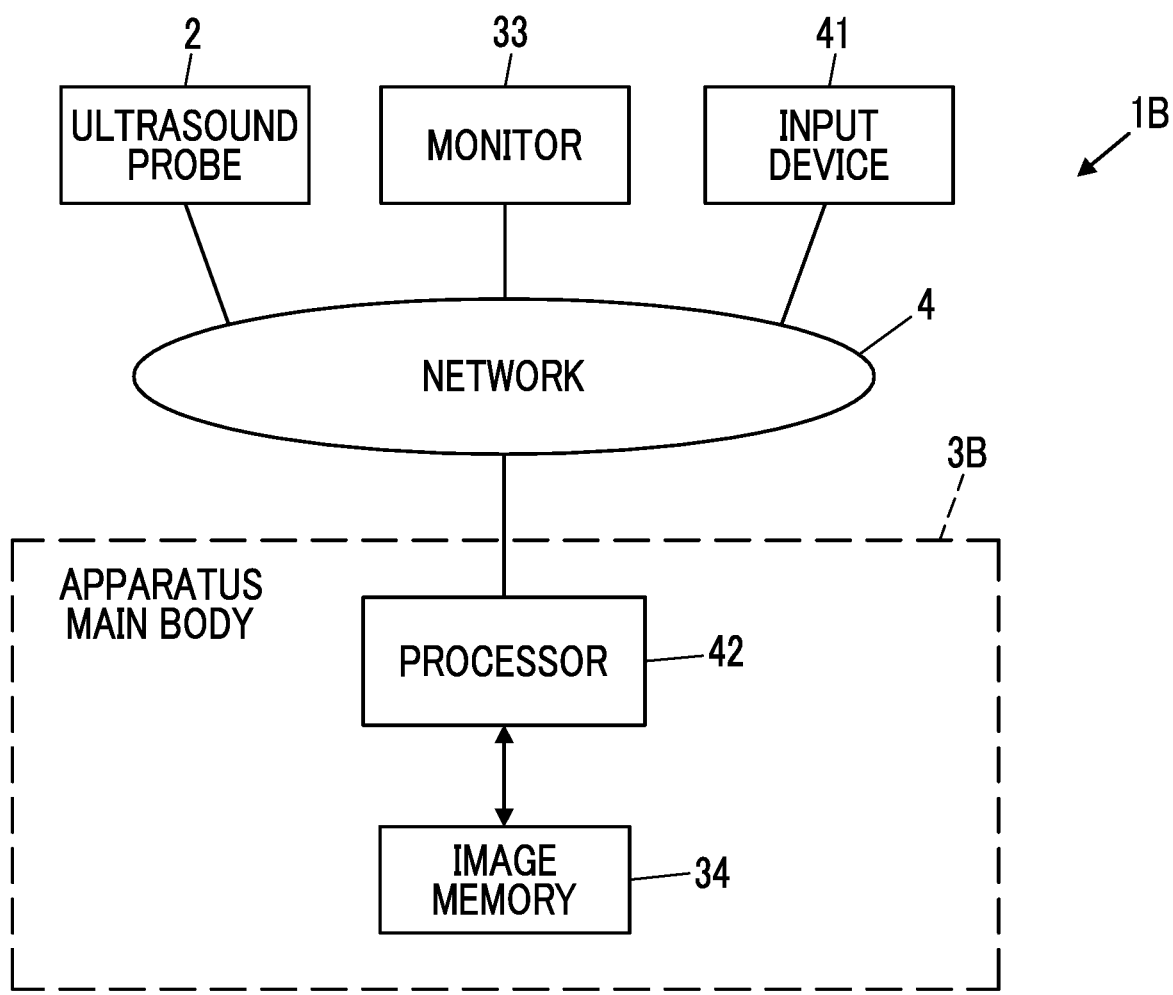
FIG. 13 is a block diagram illustrating a configuration of an ultrasound diagnostic apparatus according to an embodiment 3.

As illustrated in FIG. 13, in the ultrasound diagnostic apparatus 1B according to the embodiment 3, the ultrasound probe 2, the monitor 33, and the input device 41 are connected to the apparatus main body 3B via the network 4. The apparatus main body 3B is different from the apparatus main body 3 according to the embodiment 1 in that the monitor 33 and the input device 41 are excluded, and is configured with the image memory 34 and the processor 42.

In this way, even in a case where the ultrasound probe 2, the monitor 33, and the input device 41 are connected to the apparatus main body 3B via the network 4, as in the ultrasound diagnostic apparatus 1 according to the embodiment 1, the bladder region BR is extracted from the ultrasound image UI, the gender of the subject is determined based on the shape of the bladder region BR in a case where the area Sp of the bladder region BR is larger than the area threshold value Sth, and an observation of the next observation site that is determined according to the gender of the subject is supported. Therefore, it is possible to perform an appropriate examination corresponding to the gender of the subject without requiring the user to input the gender of the subject.

Further, since the ultrasound probe 2, the monitor 33, and the input device 41 are connected to the apparatus main body 3B via the network 4, the apparatus main body 3B can be used as a so-called remote server. Thereby, the user can perform the examination of the subject only by, for example, preparing the ultrasound probe 2, the monitor 33, and the input device 41 at hand. Thus, convenience of ultrasound diagnosis can be improved.

The ultrasound probe 2, the monitor 33, and the input device 41 may be connected to the network 4 in a wired manner or a wireless manner.

Further, for example, in a case where a portable thin computer that is called as a tablet is used as the monitor 33 and the input device 41, it is possible to more conveniently perform the urinary organ examination.

Further, the apparatus main body 3B includes the processor 42 that is used for the apparatus main body 3 according to the embodiment 1. On the other hand, the apparatus main body 3B can be configured to include the processor 42A that is used for the apparatus main body 3A according to the embodiment 2 instead of the processor 42.

Even in the embodiments 2 and 3, the bladder size calculation unit 36 may calculate, as the bladder size, the contour length of the bladder region BR or the major axis length and the minor axis length of the bladder region BR, instead of the area Sp of the bladder region BR extracted by the bladder extraction unit 35. Further, the bladder extraction unit 35 may extract the first region including the bladder region BR from the ultrasound image, and the bladder size calculation unit 36 may calculate, as the bladder size, the size of the extracted first region.

EXPLANATION OF REFERENCES 1, 1A, 1B: ultrasound diagnostic apparatus
2: ultrasound probe
3, 3A, 3B: apparatus main body
4: network
21: transducer array
22: transmission/reception circuit
23: pulser
24: amplification unit
25: AD conversion unit
26: beam former
31: image generation unit
32: display control unit
33: monitor
34: image memory
35: bladder extraction unit
36: bladder size calculation unit
37: gender determination unit
38: observation support unit
40, 40A: main body control unit
41: input device
42, 42A: processor
51: signal processing unit
52: DSC
53: image processing unit
61: reliability calculation unit
UI: ultrasound image
BR, BRm1, BRm2, BRf1, BRf2: bladder region
Cm1, Cm2, Cf1, Cf2: curved portion
Sp: area
Sth: area threshold value
PR: prostate
UT: uterus
G: guide message
BL: bladder

What is claimed is:
1. An ultrasound diagnostic apparatus comprising:
an ultrasound probe; and
a processor,
wherein the processor is configured to generate an ultrasound image obtained by imaging a subject by transmitting and receiving ultrasound beams using the ultrasound probe, extract a first region including a bladder region from the generated ultrasound image by performing an image recognition on the generated ultrasound image, calculate a size of the extracted first region, recognize a shape of the bladder region through the image recognition in a case where the calculated size of the extracted first region is larger than a size threshold value, determine a gender of the subject based on the recognized shape of the bladder region, determine a next observation site outside the bladder region to be observed next after the bladder region according to the determined gender of the subject, notify a user of the determined next observation site, guide the user to operate the ultrasound probe such that the next observation site is observed, and not determine the gender of the subject in a case where the calculated size of the first region is equal to or less than the size threshold.

2. The ultrasound diagnostic apparatus according to claim 1, wherein the processor extracts the bladder region as the first region by performing the image recognition on the generated ultrasound image.

3. The ultrasound diagnostic apparatus according to claim 1, wherein the processor extracts by performing the image recognition on the generated ultrasound image, as the first region, any one of a region surrounded by a circumscribing rectangle that circumscribes the bladder region, a region surrounded by a circumscribing ellipse that circumscribes the bladder region, a region surrounded by a circumscribing circle that circumscribes the bladder region, a region surrounded by a rectangle including the circumscribing rectangle, a region surrounded by an ellipse including the circumscribing ellipse, or a region surrounded by a circle including the circumscribing circle.

4. The ultrasound diagnostic apparatus according to claim 1, wherein the processor determines orientation and curvature of a curved portion at a lower edge of the bladder region included in the extracted first region in the generated ultrasound image by performing the image recognition on the generated ultrasound image, and determines the gender of the subject based on the determined orientation and curvature of the curved portion.

5. The ultrasound diagnostic apparatus according to claim 4, wherein the processor determines that the subject is a male in a case where a curvature radius calculated by the image recognition for the curvature on both sides of the lower edge of the bladder region in the generated ultrasound image is equal to or smaller than a curvature radius threshold value, and determines that the subject is a female in a case where the calculated curvature radius is larger than the curvature radius threshold value.

6. The ultrasound diagnostic apparatus according to claim 4, wherein the processor determines that the subject is a male in a case where the image recognition recognizes that a center portion of the lower edge of the bladder region is concavely curved downward in the generated ultrasound image, and determines that the subject is a female in a case where the image recognition recognizes that the center portion of the lower edge of the bladder region is convexly curved downward in the generated ultrasound image.

7. The ultrasound diagnostic apparatus according to claim 1, wherein the processor determines the gender of the subject by using a trained determination model, the trained determination model using machine learning technology to learn shapes of bladder regions using ultrasound images of a plurality of bladders of males and ultrasound images of a plurality of bladders of females as training data, and predicting the gender of the subject by inputting the generated ultrasound image.

8. The ultrasound diagnostic apparatus according to claim 1, wherein the processor calculates a reliability of determination of the gender of the subject, and notifies a user of the calculated reliability.

9. The ultrasound diagnostic apparatus according to claim 1, wherein the processor calculates an area of the bladder region included in the extracted first region.

10. The ultrasound diagnostic apparatus according to claim 1, further comprising:

an input device that allows a user to perform an input operation; and a monitor that displays the ultrasound image generated by the processor.

11. The ultrasound diagnostic apparatus according to claim 10, wherein the processor determines that the next observation site is a prostate in a case where it is determined that the subject is a male, and determines that the next observation site is a uterus in a case where it is determined that the subject is a female.

12. The ultrasound diagnostic apparatus according to claim 11, wherein the processor displays a guide message on the monitor to guides the user to operate the ultrasound probe such that the next observation site is visualized on the monitor.

13. The ultrasound diagnostic apparatus according to claim 12, wherein the processor guides the user to move the ultrasound probe in parallel or tilt the ultrasound probe such that the prostate is visualized on the monitor and to perform imaging of the generated ultrasound image in a case where it is determined that the subject is a male, and guides the user to rotate the ultrasound probe by 90 degrees such that the uterus is visualized on the monitor and to perform imaging of the generated ultrasound image in a case where it is determined that the subject is a female.

14. The ultrasound diagnostic apparatus according to claim 10, wherein the processor notifies the user that gender determination of the subject is not performed in a case where the size of the extracted first region is equal to or smaller than the size threshold value.

15. The ultrasound diagnostic apparatus according to claim 14, wherein the processor instructs the user to perform re-examination after a lapse of a predetermined time.

16. The ultrasound diagnostic apparatus according to claim 14,
wherein the processor displays a message on the monitor instructing the user to input information related to the gender of the subject via the input device.

17. The ultrasound diagnostic apparatus according to claim 14,
wherein the processor instructs the user to move the ultrasound probe and image an ultrasound image again such that an area of the bladder region displayed on the monitor is increased.

18. The ultrasound diagnostic apparatus according to claim 10,
wherein the processor analyzes the generated ultrasound image to automatically recognize the next observation site and displays the recognized next observation site on the monitor.

19. The ultrasound diagnostic apparatus according to claim 10,
wherein the processor notifies the user of an error in a case where the determined gender of the subject is different from the gender based on subject information of the subject that is input via the input device by the user.

20. A control method for an ultrasound diagnostic apparatus, the method comprising:
generating an ultrasound image obtained by imaging a subject by transmitting and receiving ultrasound beams using an ultrasound probe;
extracting a first region including a bladder region from the ultrasound image by performing an image recognition on the generated ultrasound image;
calculating a size of the extracted first region;
recognizing a shape of the bladder region through the image recognition in a case where the calculated size of the extracted first region is larger than a size threshold value;
determining a gender of the subject based on the recognized shape of the bladder region;
determining a next observation site outside the bladder region to be observed next after the bladder region according to the determined gender of the subject;
notifying a user of the determined next observation site;
guiding the user to operate the ultrasound probe such that the next observation site is observed; and
not determining the gender of the subject in a case where the calculated size of the first region is equal to or less than the size threshold.

* * * * *